(12) United States Patent
Olsen et al.

(10) Patent No.: US 8,324,157 B2
(45) Date of Patent: Dec. 4, 2012

(54) PREPARATION COMPRISING INSULIN, NICOTINAMIDE AND AN AMINO ACID

(75) Inventors: Helle Birk Olsen, Bagsværd (DK); Svend Havelund, Bagsværd (DK); Ulla Ribel-Madsen, Bagsværd (DK); Jeppe Sturis, Bagsværd (DK); Helle Naver, Bagsværd (DK); Morten Schlein, Bagsværd (DK); Svend Ludvigsen, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/309,134

(22) Filed: Dec. 1, 2011

(65) Prior Publication Data

US 2012/0135920 A1    May 31, 2012

Related U.S. Application Data

(63) Continuation of application No. PCT/EP2010/059069, filed on Jun. 25, 2010.

(60) Provisional application No. 61/222,168, filed on Jul. 1, 2009.

(30) Foreign Application Priority Data

Jun. 26, 2009  (EP) .................................... 09163940

(51) Int. Cl.
  *A61K 38/28*  (2006.01)
  *A61K 33/30*  (2006.01)

(52) U.S. Cl. ............................ 514/6.3; 514/5.9; 514/6.4
(58) Field of Classification Search ........................ None
  See application file for complete search history.

(56) References Cited

U.S. PATENT DOCUMENTS

| 4,205,126 | A | * | 5/1980 | Cartaya ............................ 435/2 |
|---|---|---|---|---|
| 5,382,574 | A | | 1/1995 | Jorgensen |
| 5,866,538 | A | | 2/1999 | Norup et al. |
| 6,573,237 | B2 | | 6/2003 | Rinella, Jr. |
| 2001/0031726 | A1 | * | 10/2001 | Van Antwerp et al. ........... 514/4 |
| 2004/0142852 | A1 | | 7/2004 | Younis et al. |
| 2005/0232974 | A1 | | 10/2005 | Gore |
| 2008/0039368 | A1 | | 2/2008 | Steiner et al. |

FOREIGN PATENT DOCUMENTS

| EP | 1283051 | 2/2003 |
|---|---|---|
| WO | WO 91/09617 | 7/1991 |
| WO | WO 96/10417 | 4/1996 |
| WO | WO 2008/071790 | 6/2008 |
| WO | WO2009/021955 | 2/2009 |

OTHER PUBLICATIONS

Gannon et al. Oral arginine does not stimulate an increase in insulin concentration but delays glucose disposal. The American Journal of Clinical Nutrition. 2002, vol. 76, pp. 1016-1022.*

* cited by examiner

*Primary Examiner* — Marcela M Cordero Garcia
(74) *Attorney, Agent, or Firm* — Richard W. Bork; Michael J. Brignati (57) ABSTRACT

Insulin preparations comprising an insulin compound or a mixture of two or more insulin compounds, a nicotinic compound and an amino acid.

43 Claims, 4 Drawing Sheets

PREPARATION COMPRISING INSULIN, NICOTINAMIDE AND AN AMINO ACID

CROSS REFERENCE TO RELATED APPLICATIONS

This application is a continuation of PCT/EP2010/059069, filed Jun. 25, 2010, which claimed priority of European Patent Application 09163940.1, filed Jun. 26, 2009; this application further claims priority under 35 U.S.C. §119 of U.S. Provisional 61/222,168, filed Jul. 1, 2009.

FIELD OF THE INVENTION

The present invention relates to pharmaceutical preparations comprising an insulin compound, a nicotinic compound and an amino acid.

BACKGROUND OF THE INVENTION

Diabetes mellitus is a metabolic disorder in which the ability to utilize glucose is partly or completely lost. About 5% of all people suffer from diabetes and the disorder approaches epidemic proportions.

Since the introduction of insulin in the 1920's, continuous improvements have been made in the treatment of diabetes. To help avoid high glycaemia levels, diabetic patients often practice multiple injection therapy, whereby insulin is administered with each meal. As diabetic patients have been treated with insulin for several decades, there is a major need for safe and life-quality improving insulin preparations. Among the commercially available insulin preparations, rapid-acting, intermediate-acting and prolonged-acting preparations can be mentioned.

In the treatment of diabetes mellitus, many varieties of pharmaceutical preparations of insulin have been suggested and used, such as regular insulin (such as Actrapid®), isophane insulin (designated NPH), insulin zinc suspensions (such as Semilente®, Lente®, and Ultralente®), and biphasic isophane insulin (such as NovoMix®). Human insulin analogues and derivatives have also been developed, designed for particular profiles of action, i.e. fast action or prolonged action. Some of the commercially available insulin preparations comprising such rapid acting insulin analogues include NovoRapid® (preparation of B28Asp human insulin), Humalog® (preparation of B28LysB29Pro human insulin) and Apidra® (preparation of B3LysB29Glu human insulin).

International applications WO 91/09617 and WO/9610417 (Novo Nordisk A/S) disclose insulin preparations containing nicotinamide or nicotinic acid or a salt thereof.

Most often pharmaceutical preparations of insulins are administered by subcutaneous injection. Important for the patient is the action profile of the insulin, meaning the action of insulin on glucose metabolism as a function of time from injection. In this profile, inter alia, the time of the onset, the maximum value and the total duration of action are important. In the case of bolus insulins, a variety of insulin preparations with different action profiles are desired and requested by the patients. One patient may, on the same day, use insulin preparations with very different action profiles. The action profile desired for example, depends on the time of the day and the amount and composition of the meal eaten by the patient.

Equally important for the patient is the chemical stability of the insulin preparations, for example, due to the abundant use of pen-like injection devices such as devices which contain Penfill® cartridges, in which an insulin preparation is stored until the entire cartridge is empty which may be at least 1 to 2 weeks for devices containing 1.5-3.0 ml cartridges. During storage, covalent chemical changes in the insulin structure occur. This may lead to formation of molecules which may be less active and/or potentially immunogenic such as deamidation products and higher molecular weight transformation products (dimers, polymers). Furthermore, also important is the physical stability of the insulin preparations, since long term storage may eventually lead to formation of insoluble fibrils, which are biologically inactive and potentially immunogenic.

SUMMARY OF THE INVENTION

The invention relates to insulin preparations with favourable absorption rate and favourable chemical and physical stability. The present invention relates to insulin preparations comprising human insulin and/or analogues thereof, nicotinamide or nicotinic acid and/or salts thereof, and arginine.

In one embodiment, the present invention relates to an insulin preparation comprising:
an insulin compound,
a nicotinic compound, and
arginine.

In another embodiment the insulin preparation may further comprise glutamic acid.

In another embodiment, the present invention also contemplates a method for the treatment of diabetes mellitus in a subject or for reducing the blood glucose level in a subject comprising administering to a subject or mammal an insulin preparation according to the invention.

DESCRIPTION OF THE INVENTION

The absorption after subcutaneous injection of the insulin compound in the insulin preparations of the present invention was surprisingly found to be faster than that of the reference insulin preparations. This property is useful for rapid-acting insulins, in particular in connection with a multiple injection regimen where insulin is given before each meal. With faster onset of action, the insulin can conveniently be taken closer to the meal than with conventional rapid acting insulin solutions. Furthermore, a faster disappearance of insulin probably diminishes the risk of post-meal hypoglycaemia.

The insulin preparations of the present invention are rapid-acting insulin preparations comprising an insulin compound such as insulin aspart, a nicotinic compound, such as nicotinamide and the amino acid arginine. Optionally, the insulin preparations of the present invention may comprise further amino acids such as glutamic acid. These insulin preparations have a rapid absorption profile that mimics normal physiology more closely than existing therapies. Furthermore, the insulin preparations of the present invention have chemical and physical stability suitable for commercial pharmaceutical preparations.

The insulin preparations of the present invention provide an even faster onset of action compared with existing insulin therapies. Such ultra-fast insulin preparations have the advantage of restoring first phase insulin release, injection convenience and shutting down hepatic glucose production. The insulin preparations of the present invention have a favourable absorption rate from subcutis into plasma with an increase in initial absorption rate ranging from 1.5 to 5 times, when compared to conventional preparations such as NovoRapid®, as suggested by several PK/PD experiments in pigs. This faster absorption rate may improve glycaemic control and convenience and may allow for a shift from pre-meal to post-meal dosing. The present invention is based in part, on the surprising discovery that although, the addition of nicotinamide allows the increase in absorption rate, it also has a negative effect on chemical stability by significantly increasing the amount of HMWP. The insulin preparations of the present invention have an improved chemical stability by addition of arginine, which is reflected in e.g. a reduction in the formation of dimers and polymers and desamido insulins after storage. The insulin preparations of the present invention may furthermore also have improved physical stability, which may be useful for use in pumps.

The present invention provides an insulin preparation comprising an insulin compound according to the present invention which is present in a concentration from about 0.1 mM to about 10.0 mM, and wherein said preparation has a pH from 3 to 8.5. The preparation also comprises a nicotinic compound and arginine. The preparation may further comprise protease inhibitor(s), metal ions, a buffer system, preservative(s), tonicity agent(s), chelating agent(s), stabilizers and surfactants.

In one embodiment the insulin preparations comprise a human insulin, an analogue or combinations thereof, nicotinamide and/or nicotinic acid and/or salts thereof and arginine and/or salts thereof.

In one embodiment, the insulin preparations according to the present invention comprise an aqueous solution of B28Asp human insulin, nicotinamide and arginine.

The content of B28Asp human insulin in the solutions of this invention may be in the range of 15 to 500 international units (IU)/ml, preferably in the range of 50 to 333 IU/ml, in preparations for injection. However, for other purposes of parenteral administration, the content of insulin compound may be higher.

There is also described herein an insulin preparation comprising an insulin compound, a nicotinic compound and glutamic acid.

In the present context the unit "IU" corresponds to 6 nmol.

The term "insulin aspart" refers to the human insulin analogue B28Asp human insulin.

The term "onset" refers to the time from injection until the PK curve shifts to an increase.

The term "absorption rate" refers to the slope of the PK curve.

An "insulin compound" according to the invention is herein to be understood as human insulin, an insulin analogue and/or any combination thereof.

The term "human insulin" as used herein means the human hormone whose structure and properties are well-known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

The hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

By "insulin analogue" as used herein is meant a polypeptide derived from the primary structure of a naturally occurring insulin, for example that of human insulin, by mutation. One or more mutations are made by deleting and/or substituting at least one amino acid residue occurring in the naturally occurring insulin and/or by adding at least one amino acid residue. The added and/or substituted amino acid residues can either be codable amino acid residues or other naturally occurring amino acid residues.

In one embodiment an insulin analogue comprises less than 8 modifications (substitutions, deletions, additions and any combination thereof) relative to the parent insulin, alternatively less than 7 modifications relative to the parent insulin, alternatively less than 6 modifications relative to the parent insulin, alternatively less than 5 modifications relative to the parent insulin, alternatively less than 4 modifications relative to the parent insulin, alternatively less than 3 modifications relative to the parent insulin, alternatively less than 2 modifications relative to the parent insulin.

Mutations in the insulin molecule are denoted stating the chain (A or B), the position, and the three letter code for the amino acid substituting the native amino acid. By "desB30" or "B(1-29)" is meant a natural insulin B chain or analogue thereof lacking the B30 amino acid residue, and by B28Asp human insulin is meant human insulin wherein the amino acid residue in position 28 of the B chain has been substituted with Asp.

Examples of insulin analogues are such wherein Pro in position 28 of the B chain is mutated with Asp, Lys, Leu, Val, or Ala and/or Lys at position B29 is mutated with Pro, Glu or Asp. Furthermore, Asn at position B3 may be mutated with Thr, Lys, Gln, Glu or Asp. The amino acid residue in position A21 may be mutated with Gly. The amino acid in position B1 may be mutated with Glu. The amino acid in position B16 may be mutated with Glu or His. Further examples of insulin analogues are the deletion analogues e.g. analogues where the B30 amino acid in human insulin has been deleted (des(B30) human insulin), insulin analogues wherein the B1 amino acid in human insulin has been deleted (des(B1) human insulin), des(B28-B30) human insulin and des(B27) human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position A14 is Asn, Gln, Glu, Arg, Asp, Gly or His, the amino acid in position B25 is His and which optionally further comprises one or more additional mutations are further examples of insulin analogues. Insulin analogues of human insulin wherein the amino acid residue in position A21 is Gly and wherein the insulin analogue is further extended in the C-terminal with two arginine residues are also examples of insulin analogues.

Further examples of insulin analogues include, but are not limited to: DesB30 human insulin; AspB28 human insulin; AspB28,desB30 human insulin; LysB3,GluB29 human insulin; LysB28,ProB29 human insulin; GlyA21,ArgB31, ArgB32 human insulin; GluA14,HisB25 human insulin; HisA14,HisB25 human insulin; GluA14,HisB25,desB30 human insulin; HisA14, HisB25,desB30 human insulin; GluA14,HisB25,desB27,desB28,desB29,desB30 human insulin; GluA14,HisB25,GluB27,desB30 human insulin; GluA14,HisB16,HisB25,desB30 human insulin; HisA14, HisB16,HisB25,desB30 human insulin; HisA8,GluA14, HisB25,GluB27,desB30 human insulin; HisA8,GluA14, GluB1,GluB16,HisB25,GluB27,desB30 human insulin; and HisA8,GluA14,GluB16,HisB25,desB30 human insulin.

The term "nicotinic compound" includes nicotinamide, nicotinic acid, niacin, niacin amide and vitamin B3 and/or salts thereof and/or any combination thereof.

According to the present invention, the concentration of the nicotinic compound and/or salts thereof is in the range from about 1 mM to about 300 mM or from about 5 mM to about 200 mM.

The term "arginine" or "Arg" includes the amino acid arginine and/or a salt thereof.

In one embodiment, the insulin preparation comprises 1 to 100 mM of arginine.

In one embodiment, the insulin preparation comprises 1 to 20 mM of arginine.

In one embodiment, the insulin preparation comprises 20 to 90 mM of arginine.

In one embodiment, the insulin preparation comprises 30 to 85 mM of arginine.

The term "glutamic acid" or "Glu" includes the aminoacid glutamic acid and/or a salt thereof.

In one embodiment, the insulin preparation comprises 1 to 100 mM of glutamic acid.

In one embodiment, the insulin preparation comprises 20 to 90 mM of glutamic acid.

In one embodiment, the insulin preparation comprises 30 to 85 mM of glutamic acid.

The term "pharmaceutical preparation" or "insulin preparation" as used herein means a product comprising an insulin compound, i.e., a human insulin, an analogue thereof and/or combinations thereof and a nicotinic compound and an amino acid, optionally together with other excipients such as preservatives, chelating agents, tonicity modifiers, bulking agents, stabilizers, antioxidants, polymers and surfactants, metal ions, oleaginous vehicles and proteins (e.g., human serum albumin, gelatine or proteins), said insulin preparation being useful for treating, preventing or reducing the severity of a disease or disorder by administration of said insulin preparation to a person. Thus, an insulin preparation is also known in the art as a pharmaceutical preparation or pharmaceutical composition.

The buffer may be selected from the group consisting of, but not limited to, sodium acetate, sodium carbonate, citrate, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

The insulin preparation of the present invention may further comprise other ingredients common to insulin preparations, for example zinc complexing agents such as citrate, and phosphate buffers.

Glycerol and/or mannitol and/or sodium chloride may be present in an amount corresponding to a concentration of 0 to 250 mM, 0 to 200 mM or 0 to 100 mM.

Stabilizers, surfactants and preservatives may also be present in the insulin preparations of this invention.

The insulin preparations of the present invention may further comprise a pharmaceutically acceptable preservative. The preservative may be present in an amount sufficient to obtain a preserving effect. The amount of preservative in an insulin preparation may be determined from e.g. literature in the field and/or the known amount(s) of preservative in e.g. commercial products. Each one of these specific preservatives constitutes an alternative embodiment of the invention. The use of a preservative in pharmaceutical preparations is described, for example in Remington: *The Science and Practice of Pharmacy*, 19$^{th}$ edition, 1995.

The preservative present in the insulin preparation of this invention may be as in the heretofore conventional insulin preparations, for example phenol, m-cresol and methylparaben.

The insulin preparation of the present invention may further comprise a chelating agent. The use of a chelating agent in pharmaceutical preparations is well-known to the skilled person. For convenience reference is made to Remington: *The Science and Practice of Pharmacy*, 19$^{th}$ edition, 1995.

The insulin preparation of the present invention may further comprise a stabilizer. The term "stabilizer" as used herein refers to chemicals added to polypeptide containing pharmaceutical preparations in order to stabilize the peptide, i.e. to increase the shelf life and/or in-use time of such preparations. For convenience reference is made to Remington: *The Science and Practice of Pharmacy*, 19$^{th}$ edition, 1995.

The insulin preparation of the present invention may further comprise a surfactant. The term "surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "detergent" is a synonym used for surfactants in general. The use of a surfactant in pharmaceutical preparations is well-known to the skilled person. For convenience reference is made to Remington: *The Science and Practice of Pharmacy*, 19$^{th}$ edition, 1995.

In a further embodiment the invention relates to an insulin preparation comprising an aqueous solution of an insulin compound of the present invention, and a buffer, wherein said insulin compound is present in a concentration from 0.1 mM or above, and wherein said preparation has a pH from about 3.0 to about 8.5 at room temperature (~25° C.).

The present invention also relates to methods for producing the insulin preparations of the invention.

In one embodiment, the method for making insulin preparations of the invention comprises:

a) preparing a solution by dissolving the insulin compound or a mixture of insulin compounds in water or buffer;

b) preparing a solution by dissolving a divalent metal ion in water or buffer;

c) preparing a solution by dissolving a preservative in water or buffer;

d) preparing a solution by dissolving an isotonicity agent in water or buffer;

e) preparing a solution by dissolving a surfactant and/or a stabilizer in water or buffer;

f) mixing solution a) and one or more of solutions b), c), d), and e);

Finally adjusting the pH of the mixture in f) to the desired pH followed by a sterile filtration.

The insulin preparations of the present invention can be used in the treatment of diabetes by parenteral administration. It is recommended that the dosage of the insulin preparations of this invention which is to be administered to the patient be selected by a physician.

Parenteral administration may be performed by subcutaneous, intramuscular, intraperitoneal or intravenous injection by means of a syringe, optionally a pen-like syringe. Alternatively, parenteral administration can be performed by means of an infusion pump. As a further option, the insulin preparations containing the insulin compound of the invention can also be adapted to transdermal administration, e.g. by needle-free injection or from a patch, optionally an iontophoretic patch, or transmucosal, e.g. buccal, administration.

Insulin preparations according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

In one embodiment of the invention the insulin preparation is an aqueous preparation, i.e. preparation comprising water. Such preparation is typically a solution or a suspension. In a further embodiment of the invention the insulin preparation is an aqueous solution.

The term "aqueous preparation" is defined as a preparation comprising at least 50% w/w water. Likewise, the term "aqueous solution" is defined as a solution comprising at least 50% w/w water, and the term "aqueous suspension" is defined as a suspension comprising at least 50% w/w water.

Aqueous suspensions may contain the active compounds in admixture with excipients suitable for the manufacture of aqueous suspensions.

In one embodiment, the insulin preparations of this invention are well-suited for application in pen-like devices used for insulin therapy by injection.

In one embodiment the insulin preparations of the present invention can be used in pumps for insulin administration.

The term "physical stability" of the insulin preparation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein preparations is evaluated by means of visual inspection and/or turbidity measurements after exposing the preparation filled in suitable containers (e.g. cartridges or vials) to mechanical/physical stress (e.g. agitation) at different temperatures for various time periods. Visual inspection of the preparations is performed in a sharp focused light with a dark background. The turbidity of the preparation is characterized by a visual score ranking the degree of turbidity for instance on a scale from 0 to 3 (a preparation showing no turbidity corresponds to a visual score 0, and a preparation showing visual turbidity in daylight corresponds to visual score 3). A preparation is classified physically unstable with respect to protein aggregation, when it shows visual turbidity in daylight. Alternatively, the turbidity of the preparation can be evaluated by simple turbidity measurements well-known to the skilled person. Physical stability of the aqueous protein preparations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

The term "chemical stability" of the protein preparation as used herein refers to changes in the covalent protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Increasing amounts of chemical degradation products is often seen during storage and use of the protein preparation. Most proteins are prone to deamidation, a process in which the side chain amide group in glutaminyl or asparaginyl residues is hydrolysed to form a free carboxylic acid or asparaginyl residues to form an IsoAsp derivative. Other degradations pathways involves formation of high molecular weight products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein preparation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC). Since HMWP products are potentially immunogenic and not biologically active, low levels of HMWP are advantageous.

The term "stabilized preparation" refers to a preparation with increased physical stability, increased chemical stability or increased physical and chemical stability. In general, a preparation must be stable during use and storage (in compliance with recommended use and storage conditions) until the expiration date is reached.

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenileonset diabetes, is caused by B-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

The term "pharmaceutically acceptable" as used herein means suited for normal pharmaceutical applications, i.e., not giving rise to any serious adverse events in patients.

The term "treatment of a disease" as used herein means the management and care of a patient having developed the disease, condition or disorder and includes treatment, prevention or alleviation of the disease. The purpose of treatment is to combat the disease, condition or disorder. Treatment includes the administration of the active compounds to eliminate or control the disease, condition or disorder as well as to alleviate the symptoms or complications associated with the disease, condition or disorder, and prevention of the disease, condition or disorder.

In another embodiment, an insulin analogue according to the invention is used as a medicament for delaying or preventing disease progression in type 2 diabetes.

In one embodiment of the present invention, the insulin preparation according to the invention is for use as a medicament for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders is provided.

In a further embodiment of the present invention, a method for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, coronary heart disease and other cardiovascular disorders, stroke, the method comprising administering to a patient in need of such treatment an effective amount for such treatment of an insulin preparation according to the invention, is provided.

The treatment with an insulin preparation according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity.

The treatment with an insulin preparation according to the present invention may also be combined with bariatric surgery—a surgery that influences the glucose levels and/or lipid homeostasis such as gastric banding or gastric bypass.

The production of polypeptides, e.g., insulins, is well known in the art. An insulin analogue according to the invention may for instance be produced by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999. The insulin analogue may also be produced by a method which comprises culturing a host cell containing a DNA sequence encoding the analogue and capable of expressing the insulin analogue in a suitable nutrient medium under conditions permitting the expression of the insulin analogue. For insulin analogues comprising non-natural amino acid residues, the recombinant cell should be modified such that the non-natural amino acids are incorporated into the analogue, for instance by use of tRNA mutants. Hence, briefly, the insulin analogues according to the invention are prepared analogously to the preparation of known insulin analogues.

Several methods may be used for the production of human insulin and human insulin analogues. For example three major methods which are used in the production of insulin in microorganisms are disclosed in WO2008034881. Two of these involve *Escherichia coli*, with either the expression of a large fusion protein in the cytoplasm (Frank et al. (1981) in Peptides: Proceedings of the 7th American Peptide Chemistry Symposium (Rich & Gross, eds.), Pierce Chemical Co., Rockford, Ill. pp 729-739), or use of a signal peptide to enable secretion into the periplasmic space (Chan et al. (1981) PNAS 78:5401-5404). A third method utilizes *Saccharomyces cer-* evisiae to secrete an insulin precursor into the medium (Thim et al. (1986) PNAS 83:6766-6770). The prior art discloses a number of insulin precursors which are expressed in either *E. coli* or *Saccharomyces cerevisiae*, vide U.S. Pat. No. 5,962,267, WO 95/16708, EP 0055945, EP 0163529, EP 0347845 and EP 0741188.

The insulin analogues are produced by expressing a DNA sequence encoding the insulin analogue in question in a suitable host cell by well known technique as disclosed in e.g. U.S. Pat. No. 6,500,645. The insulin analogue is either expressed directly or as a precursor molecule which has an N-terminal extension on the B-chain or a C-terminal extension on the B-chain. The N-terminal extension may have the function of increasing the yield of the directly expressed product and may be of up to 15 amino acid residues long. The N-terminal extension is to be cleaved of in vitro after isolation from the culture broth and will therefore have a cleavage site next to B1. N-terminal extensions of the type suitable in the present invention are disclosed in U.S. Pat. No. 5,395,922, and EP 765,395. The C-terminal extension may have the function of protecting the mature insulin or insulin analogue molecule against intracellular proteolytic processing by host cell exoproteases. The C-terminal extension is to be cleaved of either extra-cellularly in the culture broth by secreted, active carboxypeptidase or in vitro after isolation from the culture broth. A method for producing mature insulin and insulin analogs with C-terminal extensions on the B-chain that are removed by carboxypetidase are disclosed in WO 08037735. The target insulin product of the process may either be a two-chain human insulin or a two-chain human insulin analogue which may or may not have a short C-terminal extension of the B-chain. If the target insulin product will have no C-terminal extension of the B-chain, then said C-terminal extension should be capable of subsequently being cleaved off from the B-chain before further purification steps.

The present invention also contemplates the following non-limiting list of embodiments, which are further described elsewhere herein:

1. An insulin preparation comprising:
   an insulin compound,
   a nicotinic compound, and
   arginine.
2. The insulin preparation according to embodiment 1, wherein the insulin compound is human insulin or an insulin analog.
3. The insulin preparation according to any of the preceding embodiments, wherein the insulin compound is B28Asp human insulin.
4. The insulin preparation according to any of the preceding embodiments, wherein the insulin compound is B28LysB29Pro human insulin.
5. The insulin preparation according to any of the preceding embodiments, wherein the insulin compound is B3LysB29Glu human insulin.
6. The insulin preparation according to any of the preceding embodiments, wherein the insulin compound is present in a range selected from the following: 0.1-10.0 mM; 0.1-3.0 mM; 0.1-2.5 mM; 0.1-2.0 mM; 0.1-1.5 mM; 0.2-2.5 mM; 0.2-2.0 mM; 0.2-1.5 mM; 0.3-3.0 mM; 0.3-2.5 mM; 0.3-2.0 mM; 0.3-1.5 mM; 0.5-1.3 mM and 0.6-1.2 mM.
7. The insulin preparation according to any of the preceding embodiments, wherein the insulin compound is present in the amount from about 0.1 mM to about 10.0 mM.
8. The insulin preparation according to any of the preceding embodiments, wherein the insulin compound is present in the amount from about 0.1 mM to about 3.0 mM.
9. The insulin preparation according to any of the preceding embodiments, wherein the insulin compound is present in the amount from about 0.1 mM to about 2.5 mM.
10. The insulin preparation according to any of the preceding embodiments, wherein the insulin compound is present in the amount from about 0.1 mM to about 2.0 mM.
11. The insulin preparation according to any of the preceding embodiments, wherein the insulin compound is present in the amount from about 0.1 mM to about 1.5 mM.
12. The insulin preparation according to any of the preceding embodiments, wherein the insulin compound is present in the amount from about 0.2 mM to about 2.5 mM.
13. The insulin preparation according to any of the preceding embodiments, wherein the insulin compound is present in the amount from about 0.2 mM to about 2.0 mM.
14. The insulin preparation according to any of the preceding embodiments, wherein the insulin compound is present in the amount from about 0.2 mM to about 1.5 mM.
15. The insulin preparation according to any of the preceding embodiments, wherein the insulin compound is present in the amount from about 0.3 mM to about 3.0 mM.
16. The insulin preparation according to any of the preceding embodiments, wherein the insulin compound is present in the amount from about 0.3 mM to about 2.5 mM.
17. The insulin preparation according to any of the preceding embodiments, wherein the insulin compound is present in the amount from about 0.3 mM to about 2.0 mM.
18. The insulin preparation according to any of the preceding embodiments, wherein the insulin compound is present in the amount from about 0.3 mM to about 1.5 mM.
19. The insulin preparation according to any of the preceding embodiments, wherein the insulin compound is present in the amount from about 0.5 mM to about 1.3 mM.
20. The insulin preparation according to any of the preceding embodiments, wherein the insulin compound is present in the amount from about 0.3 mM to about 1.2 mM.
21. The insulin preparation according to any of the preceding embodiments, wherein the insulin compound is present in the amount from about 0.6 mM to about 1.2 mM.
22. The insulin preparation according to any of the preceding embodiments, wherein the insulin compound is present in the amount of about 0.6 or about 1.2 mM.
23. The insulin preparation according to any of the preceding embodiments, wherein the insulin compound is present in the amount of about 0.3 mM.
24. The insulin preparation according to any of the preceding embodiments, wherein the insulin compound is present in the amount of about 0.6 mM.
25. The insulin preparation according to any of the preceding embodiments, wherein the insulin compound is present in the amount of about 1.2 mM.
26. The insulin preparation according to any of the preceding embodiments, wherein the nicotinic compound is selected from the group consisting of nicotinamide, nicotinic acid, niacin, niacin amide and vitamin B3 and/or salts thereof and/or any combination thereof.
27. The insulin preparation according to any of the preceding embodiments, wherein the nicotinic compound is selected from nicotinamide and nicotinic acid and/or salts thereof and/or any combination thereof.
28. The insulin preparation according to any of the preceding embodiments, wherein the nicotinic compound is present in a range selected from the following: 1-300 mM; 5-200 mM; 40-120 mM, 70-140 mM or 80-130 mM.
29. The insulin preparation according to any of the preceding embodiments, comprising from about 1 mM to about 300 mM of the nicotinic compound.

30. The insulin preparation according to any of the preceding embodiments, comprising from about 8 mM to about 260 mM of the nicotinic compound.
31. The insulin preparation according to any of the preceding embodiments, comprising from about 5 mM to about 200 mM of the nicotinic compound.
32. The insulin preparation according to any of the preceding embodiments, comprising from about 1 mM to about 150 mM of the nicotinic compound.
33. The insulin preparation according to any of the preceding embodiments, comprising from about 5 mM to about 20 mM of the nicotinic compound.
34. The insulin preparation according to any of the preceding embodiments, comprising from about 20 mM to about 120 mM of the nicotinic compound.
35. The insulin preparation according to any of the preceding embodiments, comprising from about 40 mM to about 120 mM of the nicotinic compound.
36. The insulin preparation according to any of the preceding embodiments, comprising from about 20 mM to about 40 mM of the nicotinic compound.
37. The insulin preparation according to any of the preceding embodiments, comprising from about 60 mM to about 80 mM of the nicotinic compound.
38. The insulin preparation according to any of the preceding embodiments, comprising from about 70 mM to about 140 mM of the nicotinic compound.
39. The insulin preparation according to any of the preceding embodiments, comprising from about 80 mM to about 130 mM of the nicotinic compound.
40. The insulin preparation according to any of the preceding embodiments, comprising about 8 mM, 30 mM, 100 mM or 130 mM of the nicotinic compound.
41. The insulin preparation according to any of the preceding embodiments, comprising about 8 mM of the nicotinic compound.
42. The insulin preparation according to any of the preceding embodiments, comprising about 30 mM, 100 mM or 130 mM of the nicotinic compound.
43. The insulin preparation according to any of the preceding embodiments, comprising about 30 mM of the nicotinic compound.
44. The insulin preparation according to any of the preceding embodiments, comprising about 100 mM of the nicotinic compound.
45. The insulin preparation according to any of the preceding embodiments, comprising about 130 mM of the nicotinic compound.
46. The insulin preparation according to any of the preceding embodiments, comprising about 150 mM of the nicotinic compound.
47. The insulin preparation according to any of the preceding embodiments, comprising the following ranges of arginine compound: 1-100 mM, 5-120 mM, 8-85 mM, 20-90 mM, 30-90 mM, 30-85 mM, 30-60 mM or 10-40 mM.
48. The insulin preparation according to any of the preceding embodiments, comprising the following ranges of arginine compound: 1-120 mM, 8-85 mM or 1-40 mM.
49. The insulin preparation according to any of the preceding embodiments, comprising from about 1 mM to about 120 mM of arginine.
50. The insulin preparation according to any of the preceding embodiments, comprising from about 1 mM to about 100 mM of arginine.
51. The insulin preparation according to any of the preceding embodiments, comprising from about 5 mM to about 120 mM of arginine.
52. The insulin preparation according to any of the preceding embodiments, comprising from about 20 mM to about 90 mM of arginine.
53. The insulin preparation according to any of the preceding embodiments, comprising from about 30 mM to about 85 mM of arginine.
54. The insulin preparation according to any of the preceding embodiments, comprising from about 8 mM to about 85 mM of arginine.
55. The insulin preparation according to any of the preceding embodiments, comprising from about 30 mM to about 60 mM of arginine.
56. The insulin preparation according to any of the preceding embodiments, comprising from about 10 mM to about 40 mM of arginine.
57. The insulin preparation according to any of the preceding embodiments, comprising from about 1 mM to about 40 mM of arginine.
58. The insulin preparation according to any of the preceding embodiments, wherein arginine is present in a range selected from the following: 1 mM, 2 mM, 3 mM, 4 mM, 5 mM, 6 mM, 7 mM, 8 mM, 9 mM, 10 mM, 15 mM, 20 mM, 25 mM, 30 mM, 35 mM or 40 mM, 45 mM, 50 mM, 55 mM or 60 mM.
59. The insulin preparation according to any of the preceding embodiments, comprising about 1 mM of arginine.
60. The insulin preparation according to any of the preceding embodiments, comprising about 2 mM of arginine.
61. The insulin preparation according to any of the preceding embodiments, comprising about 3 mM of arginine.
62. The insulin preparation according to any of the preceding embodiments, comprising about 4 mM of arginine.
63. The insulin preparation according to any of the preceding embodiments, comprising about 5 mM of arginine.
64. The insulin preparation according to any of the preceding embodiments, comprising about 6 mM of arginine.
65. The insulin preparation according to any of the preceding embodiments, comprising about 7 mM of arginine.
66. The insulin preparation according to any of the preceding embodiments, comprising about 8 mM of arginine.
67. The insulin preparation according to any of the preceding embodiments, comprising about 9 mM of arginine.
68. The insulin preparation according to any of the preceding embodiments, comprising about 10 mM of arginine.
69. The insulin preparation according to any of the preceding embodiments, comprising about 15 mM of arginine.
70. The insulin preparation according to any of the preceding embodiments, comprising about 20 mM of arginine.
71. The insulin preparation according to any of the preceding embodiments, comprising about 25 mM of arginine.
72. The insulin preparation according to any of the preceding embodiments, comprising about 30 mM of arginine.
73. The insulin preparation according to any of the preceding embodiments, comprising about 35 mM of arginine.
74. The insulin preparation according to any of the preceding embodiments, comprising about 40 mM of arginine.
75. The insulin preparation according to any of the preceding embodiments, comprising about 45 mM of arginine.
76. The insulin preparation according to any of the preceding embodiments, comprising about 50 mM of arginine.
77. The insulin preparation according to any of the preceding embodiments, comprising about 55 mM of arginine.
78. The insulin preparation according to any of the preceding embodiments, comprising about 60 mM of arginine.
79. The insulin preparation according to any of the preceding embodiments, further comprising glutamic acid.

80. The insulin preparation according to embodiment 79, wherein glutamic acid is present in a range selected from the following: 1-100 mM, 20-90 mM, 30-90 mM, 30-85 mM or 30-50 mM.
81. The insulin preparation according to embodiment 79, comprising from about 1 mM to about 100 mM of glutamic acid.
82. The insulin preparation according to embodiment 79, comprising from about 20 mM to about 90 mM of glutamic acid.
83. The insulin preparation according to embodiment 79, comprising from about 30 mM to about 85 mM of glutamic acid.
84. The insulin preparation according to embodiment 79, comprising from about 30 mM to about 50 mM of glutamic acid.
85. The insulin preparation according to embodiment 79, comprising about 30 mM or 50 mM of glutamic acid.
86. The insulin preparation according to embodiment 79, comprising about 30 mM of glutamic acid.
87. The insulin preparation according to embodiment 79, comprising about 50 mM of glutamic acid.
88. The insulin preparation according to any of the preceding embodiments, which further comprises a metal ion, preservative agent(s), isotonicity agent(s) and stabilizer(s), detergent(s), and buffer(s).
89. The insulin preparation according to embodiment 88, wherein said buffer is Tris.
90. The insulin preparation according to embodiment 89, comprising from about 2 mM to about 50 mM of Tris.
91. The insulin preparation according to embodiment 89, comprising from about 10 mM to about 40 mM of Tris.
92. The insulin preparation according to embodiment 89, comprising from about 20 mM to about 30 mM of Tris.
93. The insulin preparation according to embodiment 89, comprising about 10 mM, 20 mM, 30 mM or 40 mM of Tris.
94. The insulin preparation according to embodiment 89, comprising about 10 mM of Tris.
95. The insulin preparation according to embodiment 89, comprising about 20 mM of Tris.
96. The insulin preparation according to embodiment 89, comprising about 30 mM of Tris.
97. The insulin preparation according to embodiment 89, comprising about 40 mM of Tris.
98. The insulin preparation according to embodiment 89, wherein the metal ion is zinc.
99. The insulin preparation according to embodiment 98, wherein less than about 6 zinc ions are present per hexamer of insulin compound.
100. The insulin preparation according to embodiment 98, wherein less than about 4 zinc ions are present per hexamer of insulin compound.
101. The insulin preparation according to embodiment 98, wherein less than about 3 zinc ions are present per hexamer of insulin compound.
102. The insulin preparation according to embodiment 98, wherein the zinc:insulin molar ratio is from about 2:6 to about 5:6.
103. The insulin preparation according to embodiment 98, wherein the zinc:insulin molar ratio is from about 2.5:6 to about 4.5:6.
104. The insulin preparation according to embodiment 98, wherein the zinc:insulin molar ratio is from about 3:6 to about 4:6.
105. The insulin preparation according to embodiment 98, wherein the zinc:insulin molar ratio is about 2:6.
106. The insulin preparation according to embodiment 98, wherein the zinc:insulin molar ratio is about 2.5:6.
107. The insulin preparation according to embodiment 98, wherein the zinc:insulin molar ratio is about 3:6.
108. The insulin preparation according to embodiment 98, wherein the zinc:insulin molar ratio is about 3.5:6.
109. The insulin preparation according to embodiment 98, wherein the zinc:insulin molar ratio is about 4:6.
110. The insulin preparation according to embodiment 98, wherein the zinc:insulin molar ratio is about 4.5:6.
111. The insulin preparation according to embodiment 98, wherein the zinc:insulin molar ratio is about 5:6.
112. The insulin preparation according to embodiment 88, wherein the stabilizer is a non-ionic detergent.
113. The insulin preparation according to embodiment 112, wherein the detergent is polysorbate 20 (Tween 20) or polysorbate 80 (Tween 80).
114. The insulin preparation according to embodiment 112, wherein the detergent is polysorbate 20 (Tween 20).
115. The insulin preparation according to embodiment 112, wherein the detergent is polysorbate 80 (Tween 80).
116. The insulin preparation according to any of embodiments 112-115, comprising from about 5 to 100 ppm, from about 10 to about 50 ppm or from about 10 to about 20 ppm of polysorbate.
117. The insulin preparation according to embodiment 88, further comprising a phenolic compound.
118. The insulin preparation according to embodiment 117, wherein said phenolic compound is present in the amount from about 0 to about 6 mg/ml or from about 0 to about 4 mg/ml.
119. The insulin preparation according to embodiment 88, further comprising m-cresol.
120. The insulin preparation according to embodiment 119, wherein m-cresol is present in the amount from about 0.5 to about 4.0 mg/ml or from about 0.6 to about 4.0 mg/ml.
121. An insulin preparation according to any of the previous embodiments, wherein the pH is neutral to weakly basic.
122. An insulin preparation according to any of the previous embodiments, wherein the pH is from about 7.0 to about 8.0.
123. An insulin preparation according to any of the previous embodiments, wherein the pH is about 7.0.
124. An insulin preparation according to any of the previous embodiments, wherein the pH is about 7.1.
125. An insulin preparation according to any of the previous embodiments, wherein the pH is about 7.2.
126. An insulin preparation according to any of the previous embodiments, wherein the pH is about 7.3.
127. An insulin preparation according to any of the previous embodiments, wherein the pH is about 7.4.
128. An insulin preparation according to any of the previous embodiments, wherein the pH is about 7.5.
129. An insulin preparation according to any of the previous embodiments, wherein the pH is about 7.6.
130. An insulin preparation according to any of the previous embodiments, wherein the pH is about 7.7.
131. An insulin preparation according to any of the previous embodiments, wherein the pH is about 7.8.
132. An insulin preparation according to any of the previous embodiments, wherein the pH is about 7.9.
133. An insulin preparation according to any of the previous embodiments, wherein the pH is about 8.0.

134. A method of reducing the blood glucose level in mammals by administering to a patient in need of such treatment a therapeutically active dose of an insulin preparation according to any of the preceding embodiments.
135. A method for the treatment of diabetes mellitus in a subject comprising administering to a subject an insulin preparation according to any of the preceding embodiments.
136. A method according to any of the preceding embodiments, for parenteral administration.
137. An insulin preparation according to any of the preceding embodiments, for use in the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders and treatment of critically ill diabetic and non-diabetic patients.

The invention is further illustrated by the following examples which are not to be construed as limiting.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Preparation of Pharmaceutical Preparations

The pharmaceutical preparations of the present invention may be formulated as an aqueous solution. The aqueous medium is made isotonic, for example, with sodium chloride or glycerol. Furthermore, the aqueous medium may contain zinc ions, for example added as zinc acetate or zinc chloride, buffers and preservatives. Arginine may be added as Arg, HCl. The pH value of the preparation is adjusted to the desired value and may be between about 3 to about 8.5, between about 3 and about 5 or about 6.5 and about 7.5 depending on the isoelectric point, pI, of the insulin in question.

TABLE 1

Composition of insulin preparations according to this invention

| | Insulin aspart (mM) | Zn (mM) | Phenol (mM) | m-cresol (mM) | NaCl (mM) | Phosphate (mM) | Tris (mM) | Glycerol (% w/v) | Arginine, HCl (mM) | Nicotinamide (mM) | Glutamic acid (mM) | pH |
|---|---|---|---|---|---|---|---|---|---|---|---|---|
| A* | 0.6 | 0.3 | 16 | 16 | 10 | 7 | | 1.6 | | | | 7.4 |
| B | 0.6 | 0.3 | 16 | 16 | 2 | 7 | | | | 130 | | 7.4 |
| C | 0.6 | 0.3 | 16 | 16 | 2 | 7 | | | 50 | 80 | 50 | 7.4 |
| D | 0.6 | 0.3 | 16 | 16 | 2 | | 7 | | | 130 | | 7.4 |
| E | 0.6 | 0.3 | 16 | 16 | 2 | | 7 | | 50 | 80 | 50 | 7.4 |
| F | 0.6 | 0.3 | 16 | 16 | 20 | 7 | | | 30 | 80 | 30 | 7.4 |
| G | 0.6 | 0.3 | 16 | 16 | 20 | | 7 | | 30 | 80 | 30 | 7.4 |
| H | 1.2 | 0.6 | 16 | 16 | 20 | 7 | | | 30 | 80 | 30 | 7.4 |
| I | 1.2 | 0.6 | 16 | 16 | 20 | | 7 | | 30 | 80 | 30 | 7.4 |
| J | 0.6 | 0.3 | 16 | 16 | 10 | | 7 | 1.3 | | 80 | | 7.4 |
| K | 0.6 | 0.3 | 16 | 16 | 10 | | 7 | 0.77 | 30 | 80 | | 7.4 |
| L | 0.6 | 0.3 | 16 | 16 | 10 | | 7 | 0.24 | 30 | 80 | 30 | 7.4 |
| M | 0.6 | 0.3 | 16 | 16 | 10 | | 7 | | 60 | 100 | | 7.4 |
| N | 0.6 | 0.3 | 16 | 16 | 10 | | 7 | 1.13 | | 100 | | 7.4 |

*Commercially available NovoRapid ®

TABLE 2

Composition of further insulin preparations according to this invention

| Preparation nr. | [Insulin aspart] mM | [Zn2+] mM | [phenol] mM | [Arg] mM | [Gly] mM | [Glu] mM | [His] mM | [Nicotinamide] mM |
|---|---|---|---|---|---|---|---|---|
| 1 | 0.6 | 0.3 | 32 | | | | | 260 |
| 2 | 0.6 | 0.3 | 32 | 10 | | | | 260 |
| 3 | 0.6 | 0.3 | 32 | 20 | | | | 260 |
| 4 | 0.6 | 0.3 | 32 | 30 | | | | 260 |
| 5 | 0.6 | 0.3 | 32 | 40 | | | | 260 |
| 6 | 0.6 | 0.3 | 32 | 50 | | | | 260 |
| 7 | 0.6 | 0.3 | 32 | | 50 | | | 260 |
| 8 | 0.6 | 0.3 | 32 | | | 50 | | 260 |
| 9 | 0.6 | 0.3 | 32 | | | | 50 | 260 |

Example 2

Analysis of Insulin Chemical Stability

Size Exclusion Chromatography

Quantitative determination of high molecular weight protein (HMWP) and monomer insulin aspart was performed on Waters insulin (300×7.8 mm, part nr wat 201549) with an eluent containing 2.5M acetic acid, 4 mM L-arginine and 20% (V/V) acetonitrile at a flow rate of 1 ml/min. and 40° C. Detection was performed with a tuneable absorbance detector (Waters 486) at 276 nm. Injection volume was 40 µl and a 600

µM human insulin standard. HMWP and concentration of the preparations were measured at each sampling point.

Reverse Phase Chromatography (UPLC)

Determination of the insulin aspart related impurities were performed on a HPLC system using a BEH RP C8 2.1×100 mm column, particle size of 1.7 µm. Waters part no 186002878, with a flow rate of 0.5 ml/min., at 40° C. detection at 220 nm. Elution was performed with a mobile phase consisting of the following:

A. 10% (w/V) acetonititrile, 2.8% (w/w) sodium sulphate, 0.3% (w/w) o-phosphoric acid, pH 3.5.

B. 70% (w/V) acetonitrile. Gradient: 0-11 min isocratic with 73%/27% of A/B, 11-12 linear change to 52%/48% A/B, 13-15 min. linear change to 73%/27% of A/B, 15-20 min. isocratic gradient at 73%/27% of A/B.

The amount of B28 iso-aspartate, desamido and other related impurities were determined as absorbance area measured in percent of total absorbance area determined after elution of the preservatives. The RP-HPLC method is equivalent to the analytical method used for quality control of Novo Nordisk marketed insulin aspart pharmaceuticals.

Addition of arginine reduces the amount of degradation products formed, especially HMWP and des-amido forms, increasing the concentration of arginine in the range 10 to 50 mM leads to further reduction of degradation. The physical stability measured as lag time in the ThT assay is reduced upon addition of arginine and is increasingly reduced when the arginine concentration is increased. The overall performance of 50 mM arginine is superior to 50 mM glycine, 50 mM glutamic acid, or 50 mM histidine regarding reduction of the formation of degradation products, as is shown in Table 3 below.

TABLE 3

Physical and chemical stability data for insulin preparations 1-9 of Table 2 (Example 1).

| Preparation nr. | Physical stability, lag time (min) in ThT assay | Chemical stability Content of degradation product (%) measured as difference between content after incubation for 2 weeks at 37° C. and at 4° C. | | | |
|---|---|---|---|---|---|
| | | B28 IsoAsp | des-amido forms | Other related impurities | HMWP |
| 1 | 160 | 1.17 | 3.67 | 1.73 | 1.36 |
| 2 | 80 | 1.30 | 3.05 | 0.82 | 0.65 |
| 3 | 80 | 1.30 | 2.49 | 0.64 | 0.34 |
| 4 | 60 | 1.31 | 2.26 | 0.79 | 0.20 |
| 5 | 60 | 1.27 | 2.27 | 0.37 | 0.19 |
| 6 | 40 | 1.36 | 1.99 | 0.47 | 0.16 |
| 7 | 100 | 1.26 | 4.72 | 2.21 | 1.11 |
| 8 | 50 | 1.39 | 3.41 | 1.07 | 0.70 |
| 9 | 0 | 1.75 | 6.99 | 2.22 | 1.01 |

Example 3

Pharmacokinetic (PK)/Pharmacodynamic (PD) Studies in LYD Pig Model and Plasma Analysis Assay PK/PD Studies in LYD Pigs The PK/PD studies were performed on domestic female pigs, LYD cross-breed, weighing between 55 and 110 kg. The pigs were catheterised into the jugular vein through an ear vein at least 2 days before start of the study. The last meal before the start of the study was served to the animals approx. 18 hours prior to the injection of the test preparation, and the animals had free access to water at all time during the fasting period and the test period.

At time 0 hours the test preparation was given subcutaneous on the lateral side of the neck. A blood sample was drawn prior dosing and at regular time intervals after dosing samples were drawn from the catheter and sampled into 1.5 ml glass tubes pre-coated with heparin. The blood samples were kept in ice water until separation of plasma by centrifugetion for 10 min. 3000 rpm at 4° C., which was done within the first 30 minutes. Plasma samples were stored at 4° C. for short time (2-3 hours) or at −18° C. for long term storage and were analysed for glucose on YSI or Konelab 30i and for insulin Aspart concentration by LOCI.

Luminescent Oxygen Channeling Immunoassay (LOCI) for Insulin Aspart Quantification The insulin Aspart LOCI is a monoclonal antibody-based sandwich immunoassay and applies the proximity of two beads, the europium-coated acceptor beads and the streptavidin coated donor-beads. The acceptor beads were coated with a specific antibody against human insulin and recognize insulin Aspart in plasma samples. A second biotinylated antibody bind specific to insulin Aspart and together with the streptavidin coated beads, they make up the sandwich. Illumination of the beads-aggregate-immunocomplex releases singlet oxygen from the donor beads which channels into the acceptor beads and triggers chemiluminescence. The chemiluminescence was measured and the amount of light generated is proportional to the concentration of insulin Aspart.

Figure 1:
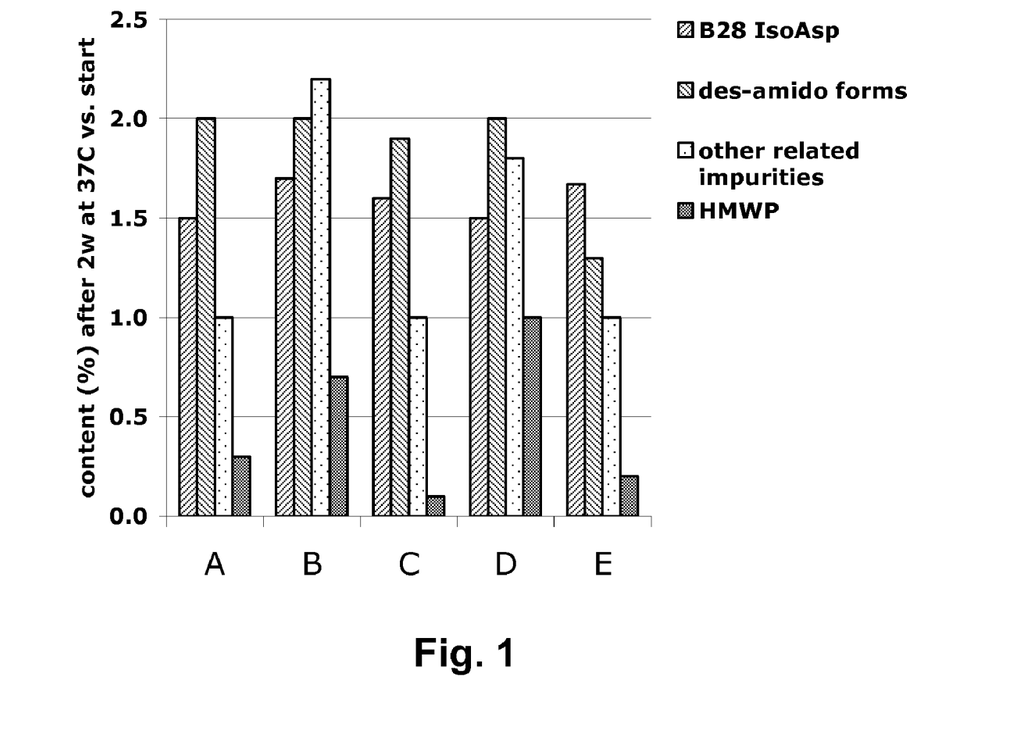
FIG. 1 shows the development in percentage of total insulin content of degradation products during 2 weeks of storage at 37° C. of preparations according to the present invention. The letter A refers to a NovoRapid® reference and remaining letters correspond to insulin aspart preparations as described in Table 1 of Example 1. Compared to the NovoRapid® preparation (preparation A), addition of nicotinamide (preparations B and D) leads to an increased formation of degradation products, whereas the combined addition of nicotinamide, glutamic acid and arginine (preparations C and E), has a mostly similar degradation pattern, with lower formation of HMWP.
Figure 2:
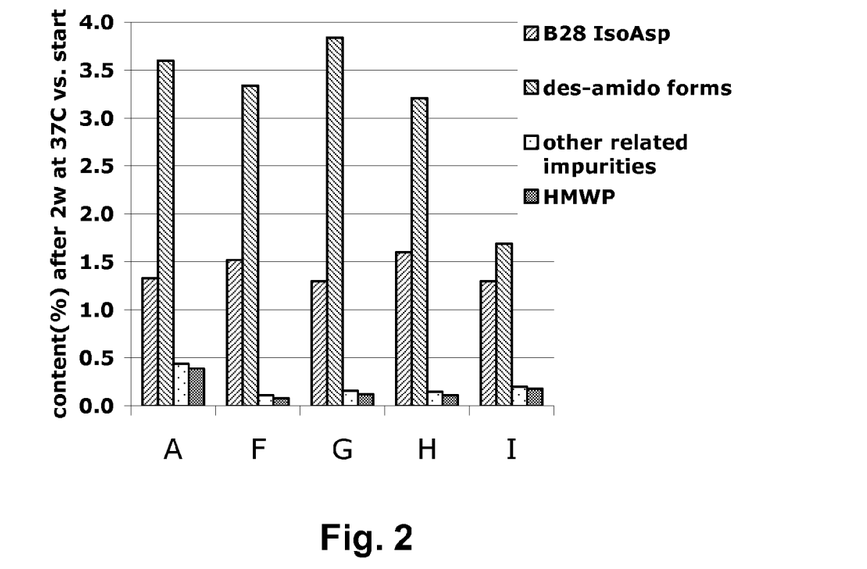
FIG. 2 shows the development in percentage of total insulin content of degradation products during 2 weeks of storage at 37° C. of preparations according to this invention. The letter A refers to a NovoRapid® reference and remaining letters correspond to insulin aspart preparations as described in Table 1 of Example 1. The combined addition of nicotinamide, glutamic acid and arginine, preparations F, G, H, and I, differing in buffer system, phosphate or tris buffer, and concentration of insulin and Zn, 0.6 mM and 0.3 mM or 1.2 mM and 0.6 mM, has a degradation pattern similar to the NovoRapid® preparation, preparation A.
Figure 3:
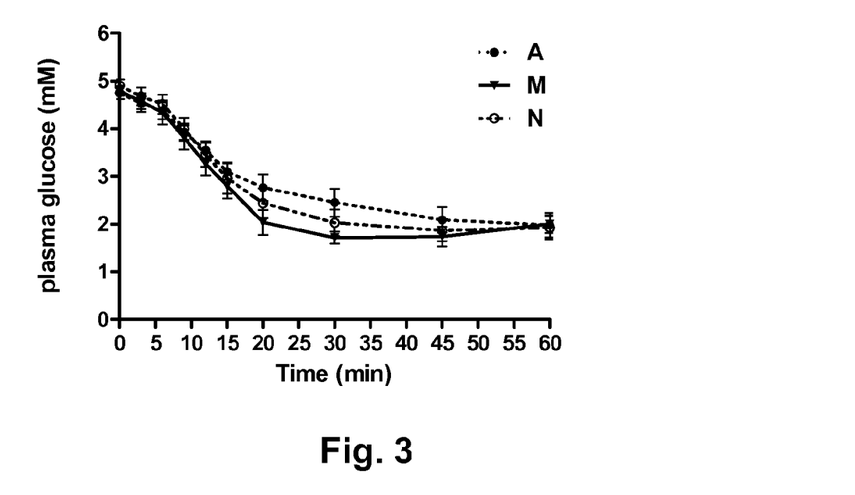
FIG. 3 shows the glucose concentration (mean+/−SEM, N=8) in plasma after subcutaneous injection in pigs of a 1 nmol/kg dose at 0 minutes of preparations according to this invention. The letter A refers to a NovoRapid® reference and remaining letters correspond to insulin aspart preparations as described in Table 1 of Example 1. Compared to the NovoRapid® preparation (preparation A) the initial rate of plasma glucose lowering is faster for the preparation with addition of nicotinamide (preparation N) and even faster for a combination of nicotinamide and arginine (preparation M).
Figure 4:
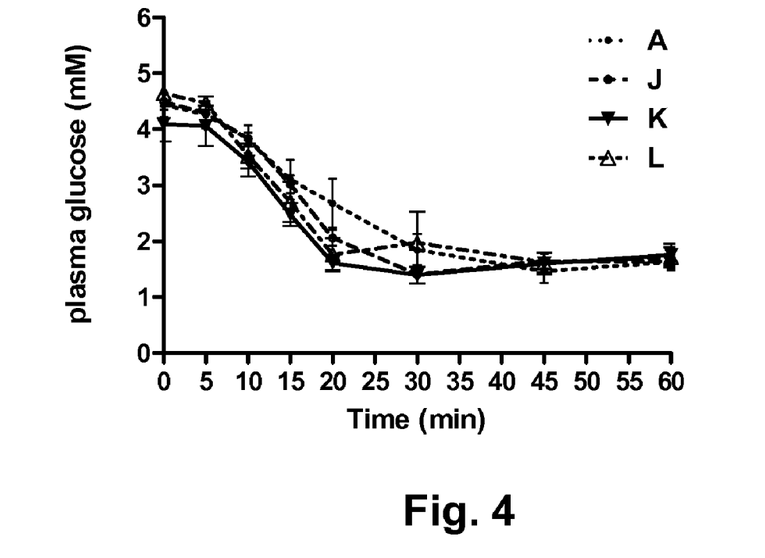
FIG. 4 shows the glucose concentration in plasma (mean+/−SEM, N=7) after subcutaneous injection in pigs of a 1 nmol/kg dose at 0 minutes of preparations according to this invention. The letter A refers to a NovoRapid® reference and remaining letters correspond to insulin aspart preparations as described in Table 1 of Example 1. Compared to the NovoRapid® preparation (preparation A), the initial rate of plasma glucose lowering is faster for a preparation with a combination of nicotinamide, arginine and glutamic acid (preparation L) and for a preparation with a combination of nicotinamide and arginine (preparation K).
Figure 5:
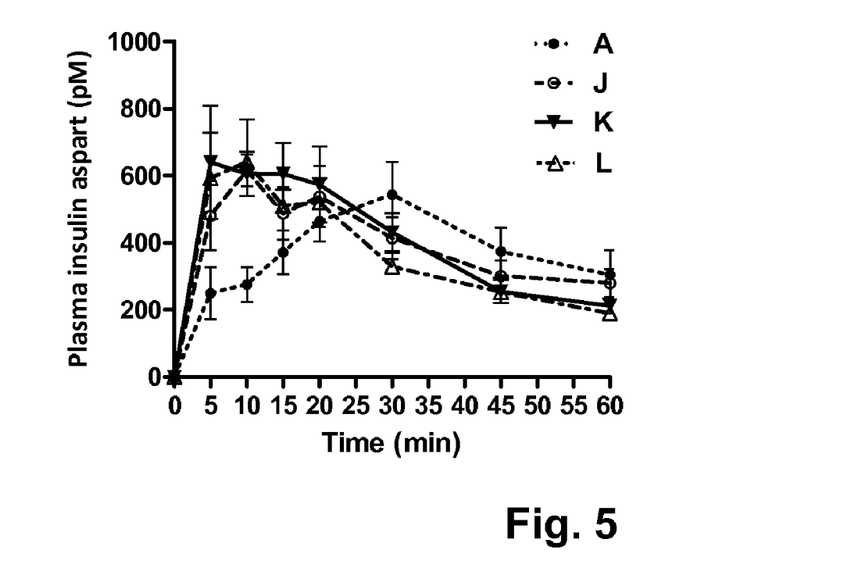
FIG. 5 shows the insulin aspart concentration in plasma (mean+/−SEM, N=7) after subcutaneous injection in pigs of a 1 nmol/kg dose at 0 minutes of preparations according to this invention. The letter A refers to a NovoRapid® reference and remaining letters correspond to insulin aspart preparations as described in Table 1 of Example 1. Compared to the NovoRapid® preparation, (preparation A), the initial absorption rate of the insulin component of the preparations with nicotinamide (preparation J), the combination of nicotinamide and arginine (preparation K), and the combination of nicotinamide, arginine and glutamic acid (preparation L) is markedly faster.

Compared to the marketed product NovoRapid®, the initial rate of plasma glucose lowering is faster for the preparations of the present invention (FIGS. 3 and 4). Likewise, when compared to NovoRapid®, the initial absorption rate of the insulin component of the preparations of the present invention, is markedly faster (FIG. 5).

Example 4

General Introduction to ThT Fibrillation Assays for the Assessment of Physical Stability of Protein Formulations Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

Figure 6:
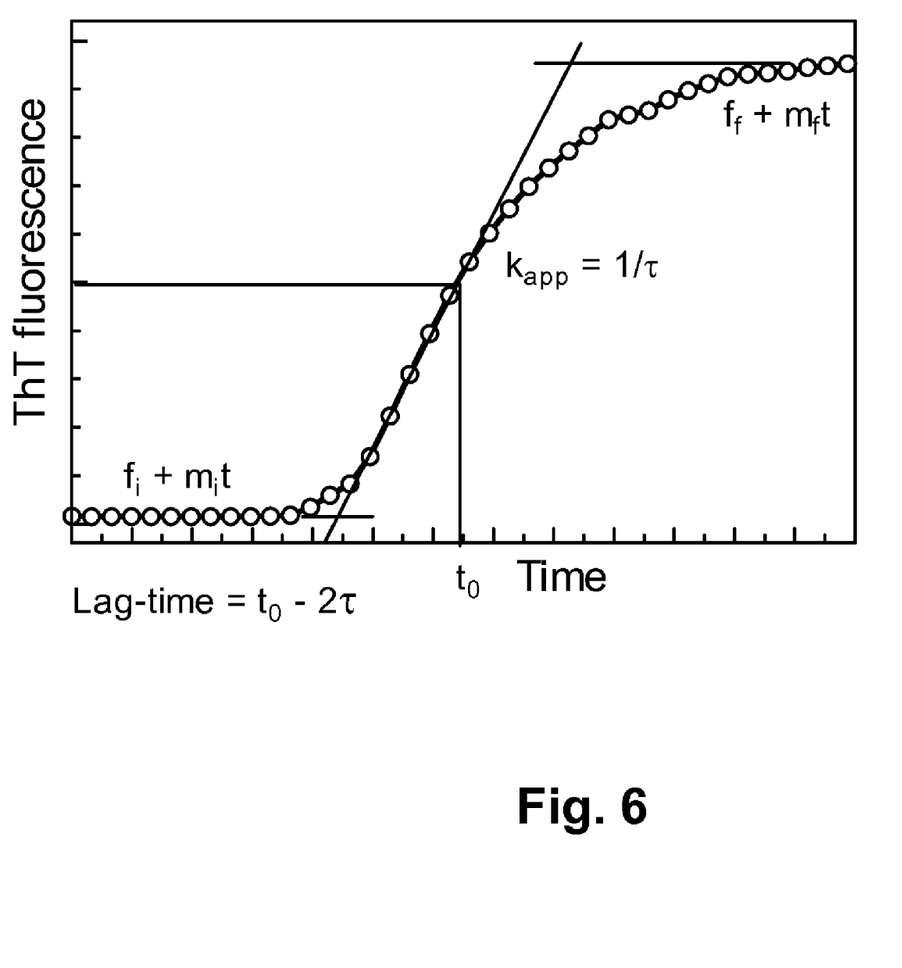
FIG. 6 shows the time course for fibril formation can be described by a sigmoidal curve using Equation 1.

The time course for fibril formation can be described by a sigmoidal curve (FIG. 6) with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in each example. The pH of the sample was adjusted to the desired value using appropriate amounts of concentrated NaOH and $HClO_4$ or HCl. Thioflavin T was added to the samples from a stock solution in $H_2O$ to a final concentration of 1 µM.

Sample aliquots of 200 µl were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader or Varioskan platereader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

Data Handling

The measurement points were saved in Microsoft Excel format for further processing and curve drawing and fitting was performed using Graph Pad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, since full sigmodial curves are not always achieved during the measurement time, lag times were here visually determined from the ThT fluorescence curve as the time point at which the ThT fluorescence is different than the background level.

Measurement of Initial and Final Concentrations

The peptide concentration in each of the tested formulations were measured both before application in the ThT fibrillation assay ("Initial") and after completion of the ThT fibrillation ("After ThT assay"). Concentrations were determined by reverse HPLC methods using a pramlintide standard as a reference. Before measurement after completion 150 µl was collected from each of the replica and transferred to an Eppendorf tube. These were centrifuged at 30000 G for 40 mins. The supernatants were filtered through a 0.22 µm filter before application on the HPLC system.

The invention claimed is:

1. A pharmaceutical formulation comprising:
B28Asp human insulin;
a nicotinic compound;
arginine;
a preservative; and
a buffer.

2. The pharmaceutical formulation of claim 1, wherein the buffer is a phosphate buffer.

3. A pharmaceutical formulation comprising:
B28Asp human insulin;
nicotinamide;
zinc;
arginine;
a preservative; and
a phosphate buffer.

4. The pharmaceutical formulation of claim 3, wherein the nicotinamide is present at a concentration ranging from about 1 mM to about 300 mM.

5. The pharmaceutical formulation of claim 4, wherein less than about 4 zinc ions are present per six B28Asp human insulin molecules.

6. The pharmaceutical formulation of claim 5, wherein the arginine is present in a concentration from about 10 mM to about 60 mM.

7. The pharmaceutical formulation of claim 6, wherein the arginine is present in a concentration ranging from about 10 mM to about 40 mM.

8. The pharmaceutical formulation of claim 7, wherein the preparation has a pH of about 7.4 or less.

9. The pharmaceutical formulation of claim 8, wherein the preparation has a pH of about 7.1.

10. The pharmaceutical formulation of claim 3, wherein the nicotinamide is present at a concentration ranging from about 80 mM to about 260 mM.

11. The pharmaceutical formulation of claim 10, wherein the arginine is present in a concentration ranging from about 10 mM to about 40 mM.

12. The pharmaceutical formulation of claim 11, wherein the preparation has a pH of about 7.4 or less.

13. The pharmaceutical formulation of claim 12, wherein less than about 4 zinc ions are present per six B28Asp human insulin molecules.

14. The pharmaceutical formulation of claim 11, wherein the preparation has a pH of about 7.1.

15. The pharmaceutical formulation of claim 14, wherein less than about 4 zinc ions are present per six B28Asp human insulin molecules.

16. An aqueous pharmaceutical formulation consisting essentially of:
B28Asp human insulin;
a nicotinic compound;
arginine;
a buffer;
zinc;
a preservative; and
an isotonicity agent.

17. The aqueous pharmaceutical formulation of claim 16, wherein the buffer is a phosphate buffer.

18. The aqueous pharmaceutical formulation of claim 17, wherein the nicotinic compound is nicotinamide.

19. The aqueous pharmaceutical formulation of claim 18, wherein the nicotinamide is present at a concentration ranging from about 80 mM to about 260 mM.

20. The aqueous pharmaceutical formulation of claim 19, wherein the arginine is present in a concentration ranging from about 10 mM to about 40 mM.

21. The aqueous pharmaceutical formulation of claim 20, wherein the preservative is selected from the group consisting of phenol, cresol, and combinations thereof, and wherein the preparation has a pH of about 7.4 or less.

22. The aqueous pharmaceutical formulation of claim 21, wherein less than about 4 zinc ions are present per six B28Asp human insulin molecules.

23. The aqueous pharmaceutical formulation of claim 21, wherein the preparation has a pH of about 7.1.

24. The pharmaceutical formulation of claim 1, wherein the buffer consists of a phosphate buffer.

25. The pharmaceutical formulation of claim 1, wherein the nicotinic compound comprises nicotinamide.

26. The pharmaceutical formulation of claim 25, wherein the nicotinamide is present at a concentration ranging from about 80 mM to about 260 mM.

27. The pharmaceutical formulation of claim 26, wherein the arginine is present in a concentration ranging from about 10 mM to about 40 mM.

28. The pharmaceutical formulation of claim 5, wherein about 3 zinc ions are present per six B28Asp human insulin molecules.

29. The pharmaceutical formulation of claim 5, wherein less than about 3 zinc ions are present per six B28Asp human insulin molecules.

30. The pharmaceutical formulation of claim 29, wherein about 2.5 zinc ions are present per six B28Asp human insulin molecules.

31. The pharmaceutical formulation of claim 13, wherein about 3 zinc ions are present per six B28Asp human insulin molecules.

32. The pharmaceutical formulation of claim 13, wherein less than about 3 zinc ions are present per six B28Asp human insulin molecules.

33. The pharmaceutical formulation of claim 32, wherein about 2.5 zinc ions are present per six B28Asp human insulin molecules.

34. The pharmaceutical formulation of claim 15, wherein about 3 zinc ions are present per six B28Asp human insulin molecules.

35. The pharmaceutical formulation of claim 15, wherein less than about 3 zinc ions are present per six B28Asp human insulin molecules.

36. The pharmaceutical formulation of claim 35, wherein about 2.5 zinc ions are present per six B28Asp human insulin molecules.

37. The aqueous pharmaceutical formulation of claim 22, wherein about 3 zinc ions are present per six B28Asp human insulin molecules.

38. The aqueous pharmaceutical formulation of claim 22, wherein less than about 3 zinc ions are present per six B28Asp human insulin molecules.

39. The aqueous pharmaceutical formulation of claim 38, wherein about 2.5 zinc ions are present per six B28Asp human insulin molecules.

40. The aqueous pharmaceutical formulation of claim 23, wherein less than about 4 zinc ions are present per six B28Asp human insulin molecules.

41. The aqueous pharmaceutical formulation of claim 40, wherein about 3 zinc ions are present per six B28Asp human insulin molecules.

42. The aqueous pharmaceutical formulation of claim 40, wherein less than about 3 zinc ions are present per six B28Asp human insulin molecules.

43. The aqueous pharmaceutical formulation of claim 42, wherein about 2.5 zinc ions are present per six B28Asp human insulin molecules.

* * * * *